United States Patent [19]
Solek

[11] Patent Number: 6,099,474
[45] Date of Patent: Aug. 8, 2000

[54] ULTRASOUND SYSTEM FOR DISPLAYING REAL TIME SIMULTANEOUS MULTIPLANE IMAGE

[76] Inventor: Roman Solek, 7068 Koll Center Pkwy., Suite 415, Pleasanton, Calif. 94566

[21] Appl. No.: 09/085,733

[22] Filed: May 27, 1998

[51] Int. Cl.$^7$ ................................................ A61B 8/14
[52] U.S. Cl. ................................. 600/459; 600/440
[58] Field of Search .................................. 600/437, 442, 600/443, 445, 459, 444, 587, 447; 128/916; 73/620, 606; 367/140

[56] References Cited

U.S. PATENT DOCUMENTS

| | | | |
|---|---|---|---|
| 4,271,706 | 6/1981 | Ledley | 128/916 |
| 4,275,597 | 6/1981 | Quedens et al. | 600/445 |
| 5,152,294 | 10/1992 | Mochizuki et al. | 128/916 |
| 5,329,496 | 7/1994 | Smith | 367/140 |
| 5,396,890 | 3/1995 | Weng | 600/443 |
| 5,460,179 | 10/1995 | Okunuki et al. | 600/444 |
| 5,503,152 | 4/1996 | Oakley et al. | 600/447 |
| 5,546,807 | 8/1996 | Oxxal et al. | 73/606 |
| 5,699,805 | 12/1997 | Seward et al. | 600/459 |
| 5,842,473 | 12/1998 | Fenster et al. | 128/916 |

*Primary Examiner*—Marvin M. Lateef
*Assistant Examiner*—Ali M. Imam
*Attorney, Agent, or Firm*—Fliesler Dubb Meyer and Lovejoy

[57] ABSTRACT

An ultrasound imaging system 20, including an ultrasound probe 22 and a console 26, creates a simultaneous multiplane image in real time. The system 20 includes an ultrasound probe 22 with an ultrasound transducer array 34. The probe 22 has a device 38 for causing the array to take 2-D images in multiple planes. The console 26 allows for the association of multiple 2-D images into a combined image.

15 Claims, 3 Drawing Sheets

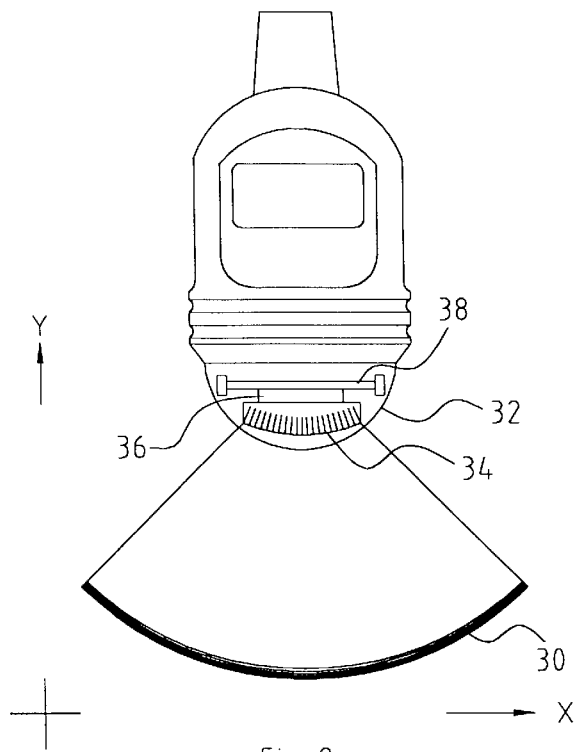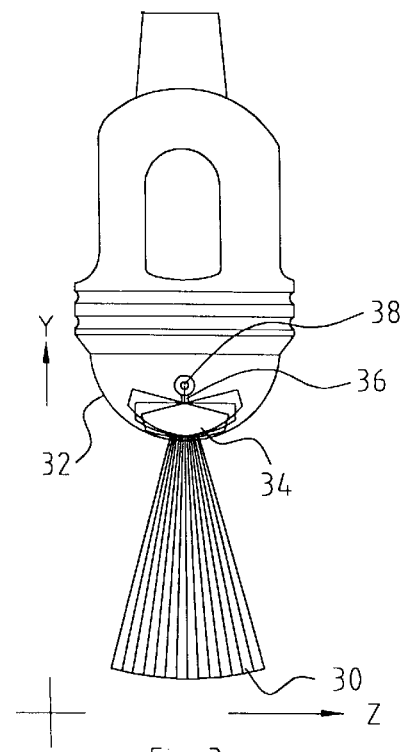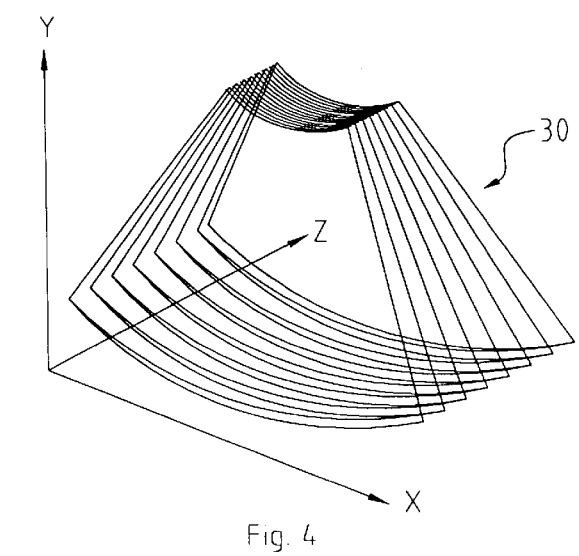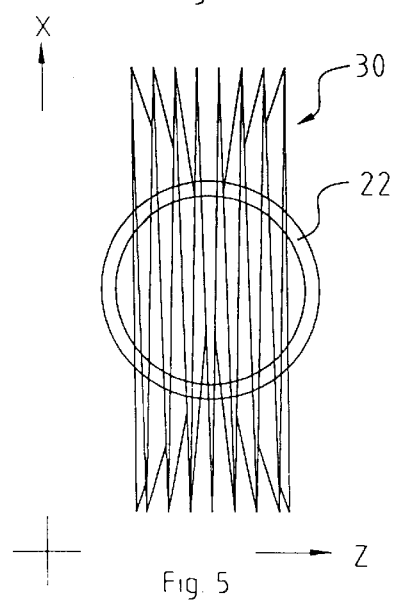

ULTRASOUND SYSTEM FOR DISPLAYING REAL TIME SIMULTANEOUS MULTIPLANE IMAGE

FIELD OF THE INVENTION

The present invention is directed to an ultrasound imaging device and in particular to one which is particularly applicable to medical applications.

BACKGROUND OF THE INVENTION

Presently available in the medical arts are a number of devices providing for different imaging modalities. Each modality has strengths and weaknesses. Generally speaking though, the devices which allow for the greatest and most enhanced imaging detail and resolution are expensive and require a considerable amount of time in order to create the image. Thus, such systems, while quite beneficial, have not been adapted to real time operation.

By way of example only, the presently existing x-ray machines are capable of rendering 3-D images which can be provided in great detail and viewed from multiple angles. These images are, however, generated over an extended period of time. Thus, they are not real time. These images have the advantage of identifying small details which can exist in various locations, throughout the tissue or organ being imaged. Thus, unlike with a single plane image which may miss important tissues due to the fact that the probe is not appropriately located, a 3-D imaging system captures an entire volume.

With a 2-D imaging system, of course the probe may be placed at multiple locations over the desired tissue to be sampled. However, if suspect tissue growths are small, positioning the probe even at successive intervals of millimeters may be not accurate enough to capture such growths which are located between the successive planes imaged by the probe.

Accordingly, it is much easier to search for and identify and thus not miss suspect tissue with a 3-D imaging system than with a 2-D or a single plane imaging system.

Thus, there is a need to provide for an imaging system which can inexpensively and in real time provide an image of an organ or tissue mass so that suspect tissues located therein can be identified.

SUMMARY OF THE INVENTION

The present invention is directed to overcoming the disadvantages of the prior art and to providing an ultrasound imaging system which can inexpensively display, in real time, simultaneous multiplane images.

The invention further includes a multiplane imaging probe. The present invention provides for an ultrasound imaging system which comprises an ultrasound probe which has an ultrasound transducer array. This instrument further includes a mechanism for causing the ultrasound transducer array to take 2-D images in multiple planes. The system further includes a device associating the 2-D images into a combined image.

The system probe includes a curved transducer array and a mechanical mechanism that causes the array to swing through an arc which is about transversed to the array.

In a further aspect of the invention, the image displayed by the system is in real time and is comprised of a plurality of side-by-side 2-D images.

The invention further includes an imaging probe which is comprised of a ultrasound probe which has an ultrasound transducer array and a pivotal mount to which the transducer array is secured. The ultrasound probe further includes a motor which can pivot the array about the pivotal mount so that the ultrasound transducer can take 2-D images in multiple planes in order to provide data which can be displayed as a real time, simultaneous, multiplane image.

Accordingly, it is an object of the present invention to provide an ultrasound imaging system which can produce a real time, simultaneous, multiplane image.

A further object of the present invention is to provide an ultrasound probe which can be secured to a ultrasound console in order to allow the console to display a real time simultaneous multiplane image.

A further object of the present invention is to provide an ultrasound system which combines a solid state curved transducer array with a mechanical mechanism for moving the array so that multiple 2-D images can be gathered for association into a combined image.

Further objects, aspects and advantages of the invention can be obtained from a review of the specification, claims and the figures.

BRIEF DESCRIPTION OF THE FIGURES

FIG. 2 depicts a top plan view of the invention with the front of the probe ultrasound cut away in order to disclose the transducer array.

FIG. 3 depicts a side view of FIG. 2 with the front portion of the ultrasound probe cut away to depict the ultrasound transducer array.

FIG. 4 depicts a perspective view of an embodiment of multiplane image of the invention.

FIG. 5 depicts an image along the Y-axis of FIG. 4.

DETAILED DESCRIPTION OF THE PREFERRED EMBODIMENT

A primary function of an ultrasound imaging system for diagnostic applications is to display, in real time, a cross-section or a slice of echogenic anatomy in the B-scan (X-Y planar) format. The geometry of the display is determined by the probe type used for imaging. The present invention adds a third axis in order to display a whole anatomy similar to an X-ray image, except that the present invention accomplishes a whole anatomy display in real time. The invention provides for a display which has a plurality of 2-D images and presents depth by placing the 2-D images in a side-by-side relationship.

Figure 1:
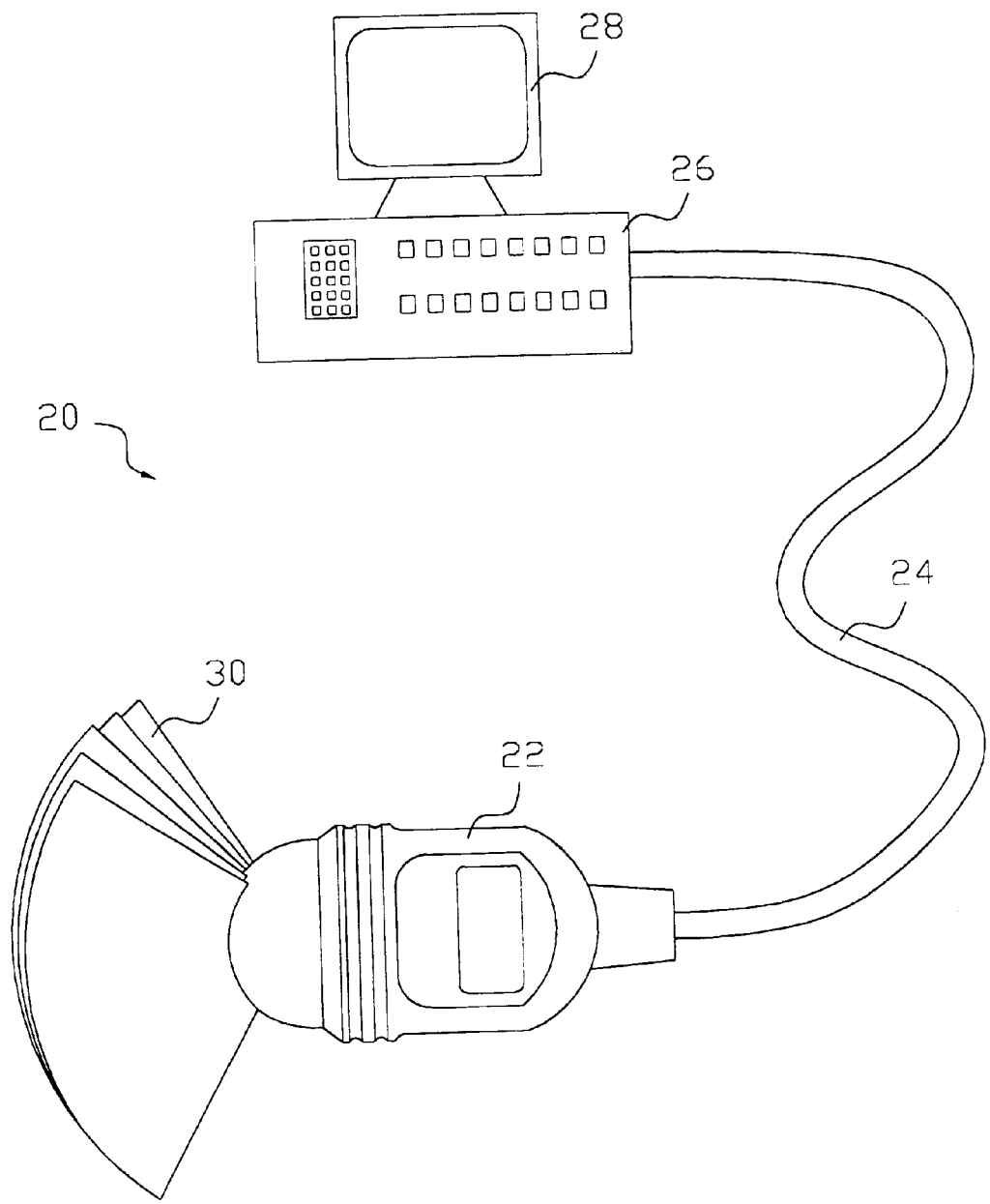
FIG. 1 depicts a top perspective view of an embodiment of the probe of the invention with hypothetical individual planes or B-scan slices, and with an embodiment of the console of the invention.

FIG. 1 depicts the ultrasound image system 20 of the invention which includes ultrasound probe 22 connected by conduit 24 to a console 26 which houses appropriate imaging software and display 28. As can be seen in FIG. 1, the probe 22 is capable of generating multiple planar images which are shown at 30. It is to be understood that these are not physical portions of the probe 22, but merely representations of ultrasound imaging slices through tissue to be imaged. FIGS. 2 and 3 depicts top and side views of the probe of FIG. 1. In these views 2 and 3, the front housing 32 has been partially removed in order to reveal a transducer array 34. In this particular embodiment, transducer array 34 is a solid state, curved, transducer array 34 which is mounted on pivoting mechanism 36 which can pivot around longitudinal pivot shaft 38. An appropriate motor is provided in the housing for causing the pivot mechanism 36 and the array 34 to pivot back and forth about pivot shaft 38 in order to provide multiple spaced apart planar images 30 as shown in FIGS. 1–5. It is to be understood that other mechanisms in addition to the pivot mechanism 36 can be employed in order to cause the transducer array 34 to move in such a fashion to describe multiple side-by-side planar images as shown. By way of example only, it would be possible, yet more costly, to have a solid state array which is electronically programmed in order to create the multiple imaging planes shown.

In this particular embodiment, the imaging probe has a tightly curved transducer array which is capable or producing a sector image in the range of 60° to 90° (X-Y scan). The X-Y scan can be pivoted plus or minus 10° to 30° from its center position (X-Z scan).

As indicated above, the display format is a composite of multiple-B scan images. In this particular embodiment, the display can contain from between 8 to 16 of the B-scan images where every B-scan image is in real time, scanning at the rate of 20–60 frames per second. In the case of 20 frames per second and 15 layers of images, the image in the center at 0° will be refinished every ½ second. At the rate of 60 frames per second and 12 layers, the time to refinish is only ⅕ of a second.

For proper geometry of the display, every layer other than the one at the center should be compensated for depth error. This compensation is accomplished through the trigometric relationship of:

$$A = B \cos a$$

Wherein:

A is the actual distance;

B is the measured distance; and a is X-Y plane angle on the Z-axis.

Figure 6:
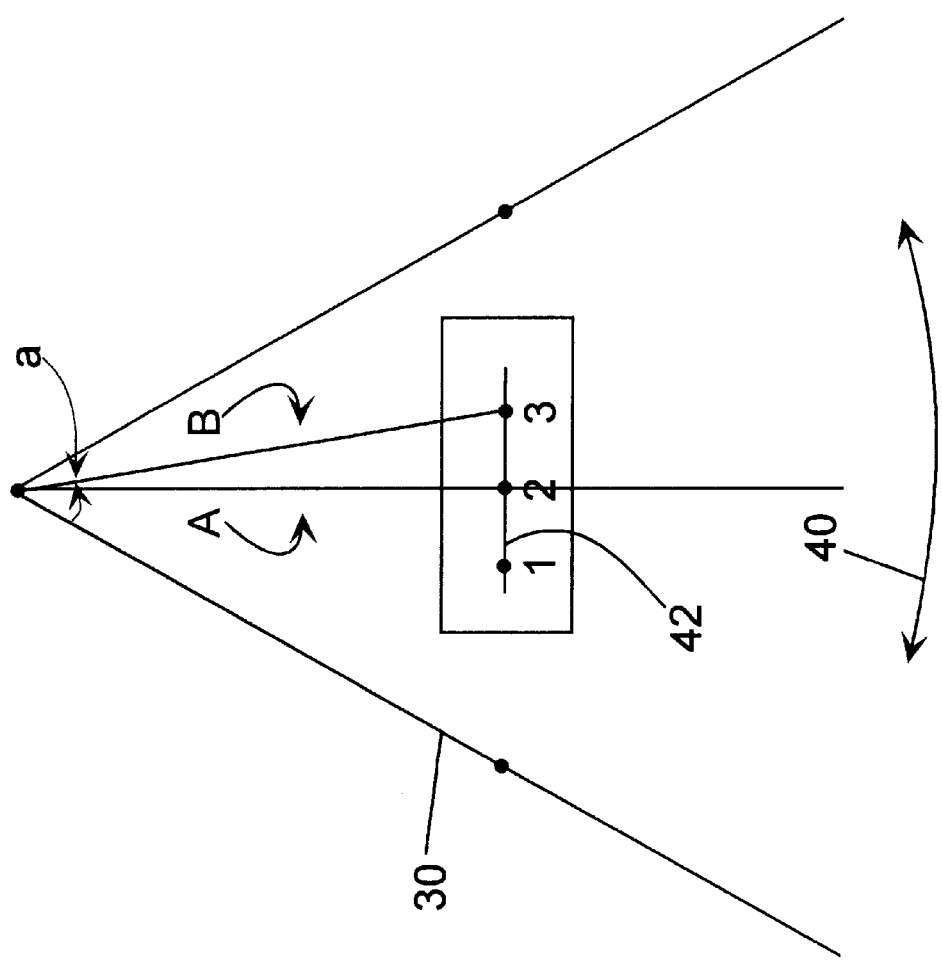
FIG. 6 depicts a view showing how an embodiment of the invention corrects for depth error.

FIG. 6 depicts this calculation. In this particular embodiment, line 42 is being imaged. In FIG. 6, the mechanical scan back and forth in the direction of arrow 40 (Z direction). The X-Y planes 30 are into the paper and only the edge of each plane is depicted. The measured distance is noted by the designation B, while the actual distance is noted by the designation A. The angle "a" is indicated as the angle between the actual distance A and the measured distance B. Using the cosign trigometric function, the actual distance A is calculated in order to compensate for the depth error and the final image includes a plurality of such X-Y planar images. The above depth error correction is made so that straight lines do not appear curved in the image.

It should be emphasized that the image created by the above system is not a 3-D image, but an image produced by associating together multiple 2-D images. A 3-D image would not be made in real time, but once made, is in great detail and could be rotated. The present image of the present invention is made in real time. However, there is not enough information provided for allowing the image to be rotated. The image of this embodiment of the invention is produced from the view point of an eye placed at the location of the probe and thus, if it were possible to rotate the image, the sides of the image would have voids due to a lack of data.

It is to be understood that with the present invention, once the real time image is made as indicated above, and tissue is identified for further study, the probe can be switched to single B-scan imaging to make a scan through a particular plane in order to obtain a high resolution image of tissues in the selected plane.

The applications of the present invention are many fold. The first application is for the real time development of a full view of an anatomy, allowing for early detection of abnormalities in the tissue. A second clinical application is for a full view of a fetus during the first trimester of pregnancy. A third clinical application facilitates the taking of biopsies. A fourth clinical application is the replacement of X-rays for mammography. Such a replacement would increase comfort during the examination as there would be no need to compress the breast between two plates. Further, an ultrasound imaging system would not be interfered with by silicon or other types of implants, and front view imaging would be possible rather than top to bottom imaging. Fifthly, a further clinical application would be for cardiology indications.

INDUSTRIAL APPLICABILITY

Ultrasound devices have emerged as unique technology among the various imaging modalities by possessing the qualities of cost effectiveness, speed, accuracy, safety and real time imaging. With the present invention, the detection of anomalies such as tumors and organs is highly improved.

Other features, aspects and objects of the invention can be obtained from a review of the figures and the claims.

It is to be understood that other embodiments of the invention can be developed and fall within the spirit and scope of the invention and claims.

What is claimed is:

1. An ultrasound imaging system comprising:

an ultrasound probe which has an ultrasound transducer;

said ultrasound probe has a means for causing the ultrasound transducer to take two-dimensional images in multiple planes which extend in outwardly directions from said ultrasound transducer;

means for associating in real time said two-dimensional images into a combined image; and said associating means includes a console and a display which depicts said two-dimensional images as a combined image of side by side two-dimensional images so as to allow simultaneous viewing through the two-dimensional images from a direction which is across said two-dimensional images.

2. The ultrasound imaging system of claim 1 wherein:

said ultrasound probe includes a solid state curved transducer array; and said causing means includes a mechanical mechanism that causes the array to swing through an arc which is about transverse to the array.

3. The system of claim 1 wherein:

said transducer is a solid state, tightly curved array.

4. The system of claim 1 wherein:

said associating means provides an image which is displayed as having a volume.

5. The system of claim 1 wherein:

said associating means has a means that corrects for depth error.

6. The system of claim 1 wherein:

said causing means includes a pivot mount upon which the transducer is mounted and a motor for causing the transducer to pivot about the pivot mount.

7. An ultrasound imaging system comprising:

an ultrasound probe which has an ultrasound transducer;

a pivot mount;

said ultrasound transducer secured to said pivot mount;

a motor that can pivot said transducer about said pivot mount so that the ultrasound transducer can take two-dimensional images in multiple planes which extend in outwardly directions from said ultrasound transducer; and a display that associates said two-dimensional images into a combined image, which display depicts said two-dimensional images as a combined real time display of side-by-side two-dimensional image so as to allow simultaneous viewing through the two-dimensional images from a direction which is across said two-dimensional images.

8. The system of claim 7 wherein:

said transducer is a solid state, tightly curved array.

9. An ultrasound imaging probe comprising:

an ultrasound transducer;

a pivot mount;

said ultrasound transducer is mounted to said pivot mount;

a motor that can pivot said transducer about said pivot mount so that the ultrasound transducer can take two-dimensional images in multiple planes which extend in outwardly directions from said ultrasound transducer; and a display that associates said two-dimensional images into a combined image, which display depicts said two-dimensional images as a combined real time display of side-by-side two-dimensional image so as to allow simultaneous viewing through the two-dimensional images from a direction which is across said two-dimensional images.

10. The probe of claim 9 wherein:

said transducer is a solid state, tightly curved array.

11. An ultrasound imaging probe comprising:

an ultrasound transducer;

a mechanism that allows the transducer to take in real time, substantially, simultaneously multiple plane images which extend in outwardly directions from said ultrasound transducer; and a display that associates said two-dimensional images into a combined image, which display depicts said two-dimensional images as a combined real time display of side-by-side two-dimensional image so as to allow simultaneous viewing through the two-dimensional images from a direction which is across said two-dimensional images.

12. The probe of claim 11 wherein:

said mechanism causes the transducer to move mechanically in order to take the multiple plane images.

13. The probe of claim 11 wherein:

said transducer is a solid state, tightly curved array.

14. A method for creating an ultrasound image comprising the steps of:

causing a plurality of two-dimensional images to be taken in multiple planes which extend in outwardly directions from an ultrasound transducer;

associating in real time the plurality of two-dimensional images together in a side-by-side relationship so as to allow simultaneous viewing through the two-dimensional images from a direction which is across said two-dimensional images.

15. The method of claim 14 including:

making adjustment in the two-dimensional images to correct errors due to depth.

\* \* \* \* \*